United States Patent
Hosono et al.

(10) Patent No.: US 11,850,272 B2
(45) Date of Patent: Dec. 26, 2023

(54) COMPOSITION COMPRISING YUZU SEED EXTRACT AND BROWN RICE EXTRACT

(71) Applicant: STARDUST HD, Inc., Tokyo (JP)

(72) Inventors: Yoshiro Hosono, Tokyo (JP); Megumi Hosono, Tokyo (JP)

(73) Assignee: STARDUST HD, Inc., Tokyo (JP)

(*) Notice: Subject to any disclaimer, the term of this patent is extended or adjusted under 35 U.S.C. 154(b) by 108 days.

(21) Appl. No.: 17/045,889

(22) PCT Filed: Apr. 10, 2019

(86) PCT No.: PCT/JP2019/015578
§ 371 (c)(1),
(2) Date: Oct. 7, 2020

(87) PCT Pub. No.: WO2019/198743
PCT Pub. Date: Oct. 17, 2019

(65) Prior Publication Data
US 2021/0138019 A1   May 13, 2021

(30) Foreign Application Priority Data
Apr. 10, 2018  (JP) ................................ 2018-075662

(51) Int. Cl.
| | | |
|---|---|---|
| A61K 36/899 | (2006.01) | |
| A61K 8/9794 | (2017.01) | |
| A61K 8/9789 | (2017.01) | |
| A61P 17/10 | (2006.01) | |
| A61P 17/00 | (2006.01) | |
| A61P 17/04 | (2006.01) | |
| A61K 8/31 | (2006.01) | |
| A61K 8/34 | (2006.01) | |
| A61K 8/36 | (2006.01) | |
| A61K 8/37 | (2006.01) | |
| A61K 8/86 | (2006.01) | |
| A61K 9/00 | (2006.01) | |
| A61K 36/752 | (2006.01) | |
| A61Q 19/00 | (2006.01) | |
| A61Q 19/08 | (2006.01) | |

(52) U.S. Cl.
CPC .............. *A61K 36/899* (2013.01); *A61K 8/31* (2013.01); *A61K 8/345* (2013.01); *A61K 8/361* (2013.01); *A61K 8/375* (2013.01); *A61K 8/86* (2013.01); *A61K 8/9789* (2017.08); *A61K 8/9794* (2017.08); *A61K 9/0014* (2013.01); *A61K 36/752* (2013.01); *A61P 17/00* (2018.01); *A61P 17/04* (2018.01); *A61P 17/10* (2018.01); *A61Q 19/007* (2013.01); *A61Q 19/08* (2013.01); *A61K 2236/333* (2013.01)

(58) Field of Classification Search
None
See application file for complete search history.

(56) References Cited

U.S. PATENT DOCUMENTS

2017/0165310 A1* 6/2017 Horiba ...................... A61P 3/04

FOREIGN PATENT DOCUMENTS

| | | |
|---|---|---|
| CN | 106132425 A | 11/2016 |
| JP | 2000-044485 A | 2/2000 |
| JP | 2001-002549 A | 1/2001 |
| JP | 2002-068953 A | 3/2002 |
| JP | 2003-012445 A | 1/2003 |
| JP | 2004-107286 A | 4/2004 |
| JP | 2004-352702 A | 12/2004 |
| JP | 2006-083150 A | 3/2006 |
| JP | 2006-206571 A | 8/2006 |
| JP | 2007-131578 A | 5/2007 |
| JP | 2007-297343 A | 11/2007 |
| JP | 2011-105652 A | 6/2011 |
| JP | 2013-082647 A | 5/2013 |
| JP | 2015-063508 A | 4/2015 |
| JP | 2016-172710 A | 9/2016 |
| JP | 2016-196429 A | 11/2016 |
| JP | 2017-014167 A | 1/2017 |
| JP | 2017-193506 A | 10/2017 |
| JP | 2017-214349 A | 12/2017 |
| JP | 2018-002607 A | 1/2018 |
| JP | 2018-035145 A | 3/2018 |
| KR | 1999-0070334 A | 9/1999 |
| KR | 10-2003-0017928 A | 3/2003 |
| KR | 10-2006-0025278 A | 3/2006 |
| KR | 10-2006-0104807 A | 10/2006 |
| KR | 10-2009-0080153 A | 7/2009 |
| KR | 10-2010-0021088 A | 2/2010 |
| KR | 10-2016-0000093 A | 1/2016 |
| KR | 101685581 B1 | 12/2016 |
| KR | 10-2017-0029143 A | 3/2017 |
| KR | 10-2017-0055619 A | 5/2017 |
| WO | WO-2015/122067 A1 | 8/2015 |

OTHER PUBLICATIONS

Notice of Allowance dated Apr. 27, 2021, in KR 10-2020-7028165.
Office Action dated Feb. 18, 2021 in KR 10-2020-7028165.
"[Experience] Combi AtopiAid series for relaxing and protecting atopic skin-atopic skin-relaxing lotion and atopic skin-repairing cream," https://bettychen.pixnet.net/blog/post/42441037, May 31, 2015, with partial English translation.
"CEREMIND ceramide can build skin barrier function," Dr. Deung's Skin Clinic, Jul. 12, 2016, https://skin22506065.pixnet.net/blog/post/391483411, with English translation.
"Skin improver and its manufacturing method," Enterprise Science and Technology & Development, Jun. 15, 1996, with partial English translation.

(Continued)

*Primary Examiner* — Russell G Fiebig
(74) *Attorney, Agent, or Firm* — Foley & Lardner LLP

(57) ABSTRACT

The present invention relates to a composition comprising an aqueous solvent extract of yuzu seeds and an aqueous solvent extract of brown rice; and a method for treating or suppressing various symptoms of skin problems and allergic skin diseases including atopic dermatitis using the composition.

16 Claims, 2 Drawing Sheets

(56) References Cited

OTHER PUBLICATIONS

"Wisdom of life—secret to whitening skin with brown rice," https://zhcn.facebook.com/notes/122926901117852, Apr. 11, 2011, with partial English translation.
Lynde et al., "Moisturizers and Ceramide-containing Moisturizers May Offer Concomitant Therapy with Benefits," The Journal of Clinical and Aesthetic Dermatology, Mar. 7, 2014, 7(3):18-26.
Office Action dated Apr. 6, 2020 in TW 108112558.
Office Action dated Sep. 29, 2020 in CN 201980004867.5.
Oryza Oil & Fat Chemical Co., Ltd., "Yuzu Seed Extract," Aug. 7, 2011, ver. 3, 1-26.
International Search Report dated Jun. 11, 2019, in PCT/JP2019/015578.
Supplementary European Search Report dated Nov. 17, 2021 in EP 19786179.2.

* cited by examiner

COMPOSITION COMPRISING YUZU SEED EXTRACT AND BROWN RICE EXTRACT

CROSS-REFERENCE TO RELATED APPLICATIONS

This application is the U.S. National Stage of PCT/JP2019/015578, filed Apr. 10, 2019, which claims priority to JP 2018-075662, filed Apr. 10, 2018.

TECHNICAL FIELD

The present invention relates to a composition comprising an aqueous solvent extract of yuzu seeds and an aqueous solvent extract of brown rice.

BACKGROUND ART

Consumers of cosmetics having diseases such as atopic dermatitis have such sensitive skin that the skin becomes red and inflamed if commonly formulated cosmetics are used.

In this connection, cosmetics containing a plant-derived ingredient such as a yuzu seed extract have been proposed (for example, Patent Literature 1).

Further, cosmetics containing γ-aminobutyric acid-enriched rice ground and fermented by yeast with the addition of water have been proposed (for example, Patent Literature 2).

However, even these cosmetics have caused inflammation in consumers having sensitive skin.

Thus, in this field, cosmetics that can be used at ease even by persons having diseases such as atopic dermatitis and hence sensitive skin have still been desired.

CITATION LIST

Patent Literature

Patent Literature 1: Japanese Patent Laid-Open No. 2003-12445
Patent Literature 2: Japanese Patent Laid-Open No. 2018-2607

SUMMARY OF INVENTION

Technical Problem

An object of the present invention is to provide safer cosmetics that can be used at ease even by persons having sensitive skin.

Another object of the present invention is to provide novel means capable of treating or relieving, or alleviating or suppressing skin problems such as atopic dermatitis.

Solution to Problem

The present inventors have extensively conducted studies for solving the above-described problem, and resultantly found that by applying a composition containing a combination of an aqueous solvent extract of yuzu seeds and an aqueous solvent extract of brown rice to affected areas from skin problems such as atopic dermatitis, symptoms of such problems can be treated or relieved, or alleviated or suppressed. Further, the present inventors have found that as cosmetics such as moisturizing agents, the composition can be used at ease even by persons having sensitive skin.

The present invention is based on the above-mentioned findings, and includes the following inventions.

[1] A composition comprising:
   an aqueous solvent extract of yuzu seeds; and
   an aqueous solvent extract of brown rice.
[2] The composition according to [1], wherein the brown rice is germinated brown rice or non-germinated brown rice.
[3] The composition according to [1] or [2], wherein the aqueous solvent is one or a combination of two or more selected from the group consisting of water and alcohols.
[4] The composition according to any one of [1] to [3], wherein the composition is used for improving dryness of skin.
[5] The composition according to any one of [1] to [3], wherein the composition is used for improving itching of skin from allergic dermatitis or the like.
[6] The composition according to any one of [1] to [3], wherein the composition is used for improving acne.
[7] The composition according to any one of [1] to [3], wherein the composition is used for improving atopic dermatitis.
[8] The composition according to any one of [1] to [3], wherein the composition is used for improving wrinkling.
[9] The composition according to any one of [1] to [8], wherein the composition is a pharmaceutical composition or a cosmetic composition.
[10] A method for producing a composition comprising an aqueous solvent extract of yuzu seeds and an aqueous solvent extract of brown rice, the method comprising the steps of:
   extracting yuzu seeds with an aqueous solvent to obtain an aqueous solvent extract; and
   extracting brown rice with an aqueous solvent to obtain an aqueous solvent extract.
[11] The method according to [10], comprising the steps of:
   extracting yuzu seeds with an aqueous solvent to obtain an aqueous solvent extract; and
   extracting brown rice with the aqueous solvent extract to obtain an extraction liquid.
[12] The method according to [10] or [11], wherein the brown rice is germinated brown rice or non-germinated brown rice.
[13] A composition to be used in a method for treating or relieving dryness of skin, itching of skin from allergic dermatitis or the like, acne, atopic dermatitis or wrinkling, the composition comprising an aqueous solvent extract of yuzu seeds and an aqueous solvent extract of brown rice.
[14] A method for treating or relieving dryness of skin, itching of skin from allergic dermatitis or the like, acne, atopic dermatitis or wrinkling, the method comprising applying to an affected area a composition comprising an aqueous solvent extract of yuzu seeds and an aqueous solvent extract of brown rice.
[15] Use of an aqueous solvent extract of yuzu seeds and an aqueous solvent extract of brown rice in a method for producing a composition for treating or relieving dryness of skin, itching of skin from allergic dermatitis or the like, acne, atopic dermatitis or wrinkling.

This specification includes the contents of the specification and/or drawings of Japanese Patent Application No. 2018-075662 based on which priority of the present application is claimed.

All publications, patents and patent applications cited in this specification are hereby incorporated by reference in their entirety.

Advantageous Effects of Invention

According to the present invention, it is possible to provide safer cosmetics that can be used at ease even by persons having sensitive skin.

Further, according to the present invention, it is possible to provide new means capable of treating or relieving, or alleviating or suppressing skin problems such as atopic dermatitis.

DESCRIPTION OF EMBODIMENT

Figure 1:
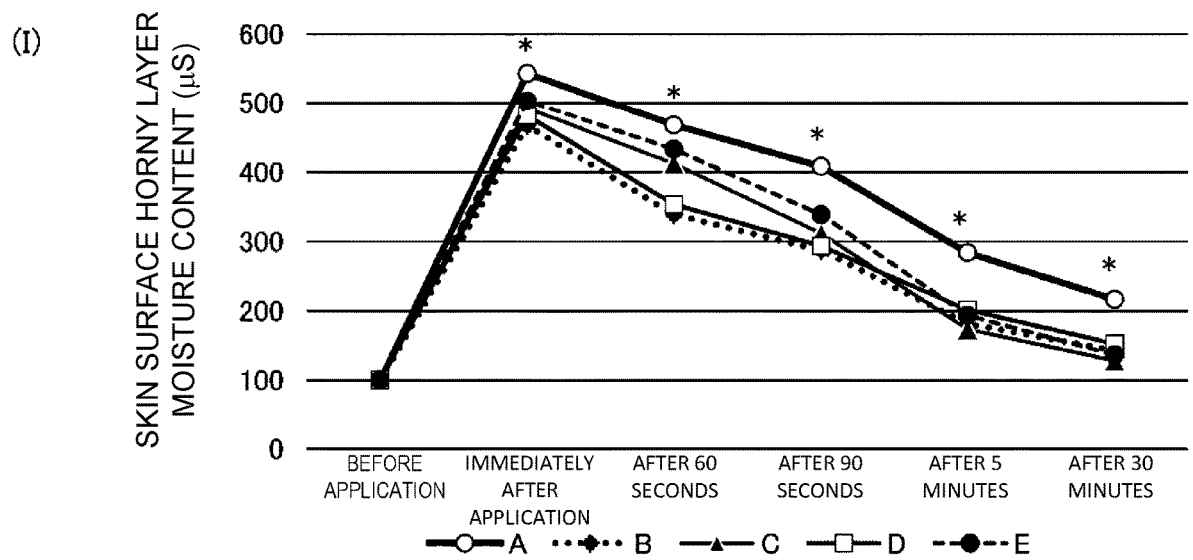
FIG. 1(I) is a graph chart showing the results of measuring the skin surface horny layer moisture content before and after application of extracts A to E, where A is an aqueous solvent extract of a yuzu seed whole (dry weight: 350 g) and a non-germinated brown rice whole (dry weight: 30 g), B is an aqueous solvent extract of a non-germinated brown rice whole (dry weigh: 30 g), C is an aqueous solvent extract of a yuzu seed whole (dry weight: 350 g), D is an aqueous solvent extract of a non-germinated brown rice whole (dry weight: 50 g) and E is an aqueous solvent extract of a yuzu seed whole (dry weight: 500 g) (*: P<0.05 (vs each of B, C, D and E), t-test), and FIG. 1(II) is a graph chart showing the results of measuring the skin surface horny layer moisture content before and after application of the aqueous solvent extract of the yuzu seed whole and the non-germinated brown rice whole before and after continuous use of the extract (for 2 weeks) (*: P<0.05 (vs a value before continuous use), t-test).
Figure 1:
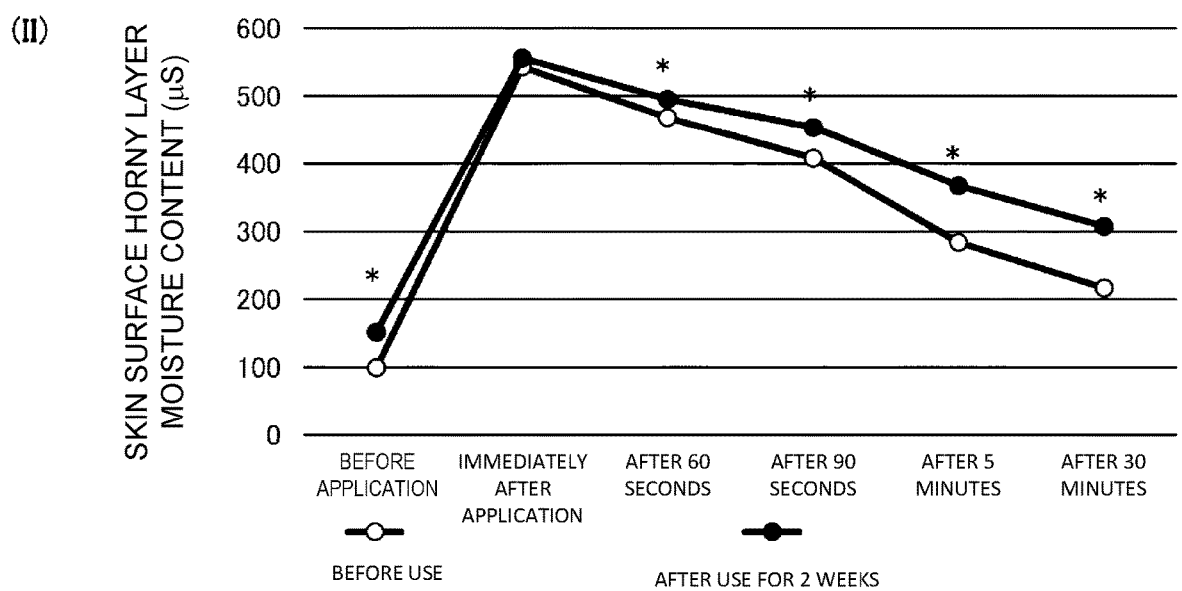

1. Aqueous Solvent Extract of Yuzu Seeds

In the present invention, the "yuzu" includes plants belonging to the yuzu (*Citrus junos*) species of *Citrus* genus, and those having the scientific name of *Citrus junos* can be used. Those available in the Japanese and overseas markets can be used, and there is no particular limitation on varieties.

In the present invention, the term "yuzu seeds" means seeds taken out from yuzu fruit, and the form thereof is not particularly limited. The yuzu seeds may be those subjected to treatment such as crushing, grinding, compression or cutting, and are preferably whole seeds taken out from the fruit (herein, sometimes referred to as a "yuzu seed whole"). As yuzu seeds, not only seeds from fully ripened fruit (so called "kiyuzu" (yellow yuzu), which is generally put on the market around October to December in Japan), but also seeds from underripe fruit (so called "aoyuzu" (green yuzu), which is generally put on the market around July to October in Japan) can be used. After being taken out from fruit, yuzu seeds may be washed for removing fruit pulp and the like. Preferably, the seeds are used without being subjected to a washing step. The yuzu seeds taken out from fruit may be subjected to a drying step.

The yuzu seeds contain pectin, hesperidin, flavonoid, limonene and the like.

In the present invention, examples of the "aqueous solvent" include water, hydrophilic organic solvents and combinations thereof. Examples of the hydrophilic organic solvent include, but are not limited to, lower alcohols (for example, ethanol, methanol and isopropanol), isostearyl alcohol, acetone and acetonitrile. The "aqueous solvent" is preferably a mixed liquid of water and a hydrophilic organic solvent, especially preferably a mixed liquid of water and ethanol. The mixing ratio of water and the hydrophilic organic solvent in the mixed liquid is not particularly limited, and the water and the hydrophilic organic solvent can be mixed at a weight ratio selected from the range of 6 to 9:1 to 4, preferably 7 to 9:1 to 3, more preferably 8 to 9:1 to 2. For example, in the present invention, a 20% ethanol aqueous solution can be suitably used as the "aqueous solvent". As the aqueous solvent, the following aqueous solvent extract of brown rice may be used.

In the present invention, the term "aqueous solvent extract of yuzu seeds" means an extract obtained by mixing the yuzu seeds and the aqueous solvent. The mixing of the yuzu seeds and the aqueous solvent can be performed by immersing the yuzu seeds in the aqueous solvent at 1° C. to 100° C., preferably at 1° C. to 50° C., more preferably at 1° C. to 25° C., further more preferably at a lower temperature, for example, a temperature of 1° C. to 10° C., especially preferably 3° C. to 7° C., for example 5° C.±1° C. or 5° C., for 1 hour to 2200 hours, preferably 18 hours to 100 hours, for example, 96 hours. If necessary, shaking, stirring and/or application of pressure may be added. Methods for shaking, stirring and/or application of pressure can be appropriately determined by the practitioner. For the amounts of the yuzu seeds and the aqueous solvent, the aqueous solvent can be used in an amount selected from the range of 1 part by weight to 100 parts by weight, preferably 1 part by weight to 50 parts by weight, more preferably 1 part by weight to 10 parts by weight, further more preferably 1 part by weight to 5 parts by weight, per part by weight of the yuzu seeds. For example, in the present invention, the aqueous solvent can be used in an amount of 2 parts by weight to 4 parts by weight per part by weight of the yuzu seeds. For example, the aqueous solvent can be used in an amount of 750 mL to 1500 mL per 350 g of the yuzu seeds.

Together with the yuzu seeds, the following brown rice may be added to the aqueous solvent and extracted in parallel as described below.

Subsequently, the mixture is subjected to solid-liquid separation, and the liquid part is recovered to obtain an aqueous solvent extract of yuzu seeds. The solid-liquid separation can be performed by a common method, and it is possible to use means such as centrifugation or filtration (but not limited to those). The resulting aqueous solvent extract of yuzu seeds can be concentrated if necessary. The concentration of the extract can be performed by a common method such as distillation. Further, the resulting aqueous solvent extract of yuzu seeds can be dried or frozen if necessary. The drying of the extract can be performed by a method that is commonly used for removal of a solvent, and examples thereof include drying under reduced pressure, air-blow drying, drying by heating, air drying and freeze drying.

2. Aqueous Solvent Extract of Brown Rice

In the present invention, the term "brown rice" means rice that is free of chaff but is not polished. There is no particular limitation on varieties of rice, and one available in the Japanese and overseas markets can be used.

In the present invention, the form of "brown rice" is not particularly limited, and may be one obtained by subjecting the entirety or a part of the brown rice to treatment such as crushing, grinding, compression or cutting (for example, rice bran). Whole brown rice (herein, sometimes referred to as a "brown rice whole") is preferable. As the brown rice, one that is germinated (hereinafter, referred to as "germinated brown rice") or one that is non-germinated (hereinafter, referred to as "non-germinated brown rice") can be used, and it is preferable to use non-germinated brown rice.

The germinated brown rice can be obtained by immersing brown rice, preferably unwashed brown rice in water or an aqueous solvent, and storing them at a temperature of 10 to 45° C., preferably 30 to 42° C., more preferably 35 to 40° C., for example 37° C.±1° C., preferably 37° C., for 4 hours to 3 days, preferably 1 day to 2 days. During the storage period, water may be renewed. Renewing the water is aimed at removing impurities, bacteria, dust, contaminants and the like, which are generated as the brown rice germinates. In the present invention, the "germinated brown rice" is preferably one sprouting to 0.2 to 1 mm, preferably about 0.5 mm. If the sprout excessively grows, or the root comes into existence, it may be impossible to sufficiently obtain a desired effect of the present invention because nutrients are consumed for growth of the sprout or the root. The germinated brown rice may contain non-germinated brown rice. The non-germinated brown rice may be present in a ratio of less than 10%, for example less than 7%, preferably less than 5%, more preferably less than 3%, especially preferably less than 1% to the entire recovered brown rice.

The germinated brown rice contains γ-aminobutyric acid (GABA), minerals, vitamins (e.g. vitamin C), amino acids (e.g. aspartic acid and glutamic acid), dietary fibers, tocotrienol, oryzanol, phytic acid, ferulic acid, phytosterol, tocopherol, octacosanol, inositol, phospholipid, sphingolipid, triglyceride and the like.

The non-germinated brown rice can be obtained by immersing brown rice, preferably unwashed brown rice in water, and storing them at a temperature of 10 to 45° C., preferably 30 to 42° C., more preferably 35 to 40° C., for example 37° C.±1° C., preferably 37° C., for 4 hours to 3 days, preferably 1 day to 2 days. During the storage period, water may be renewed. Renewing the water is aimed at removing impurities, bacteria, dust, contaminants and the like, which are generated as the brown rice germinates. In the present invention, the "non-germinated brown rice" is preferably one immediately before germination (sprout protrusion observed), for example one having an expanded germ. If the germ is not expanded, or germination has already occurred, it may be impossible to sufficiently obtain a desired effect of the present invention because nutrients are not produced, or consumed. The non-germinated brown rice may contain germinated brown rice. The germinated brown rice may be present in a ratio of less than 10%, for example less than 7%, preferably less than 5%, more preferably less than 3%, especially preferably less than 1% to the entire recovered brown rice.

The non-germinated brown rice contains γ-aminobutyric acid (GABA), minerals, vitamins (e.g. vitamin C), amino acids (e.g. aspartic acid and glutamic acid), dietary fibers, tocotrienol, oryzanol, phytic acid, ferulic acid, phytosterol, tocopherol, octacosanol, inositol, phospholipid, sphingolipid, triglyceride and the like.

In the present invention, the term "aqueous solvent extract of brown rice" means an extract obtained by mixing the brown rice and the aqueous solvent. As the aqueous solvent, any of those described above can be used. Further, as the aqueous solvent, the aqueous solvent extract of yuzu seeds may be used. The mixing of the brown rice and the aqueous solvent can be performed by storing the brown rice in the aqueous solvent at 1° C. to 100° C., preferably at 1° C. to 50° C., more preferably at 1° C. to 25° C., further more preferably at a lower temperature, for example, a temperature of 1° C. to 10° C., especially preferably 3° C. to 7° C., for 4 hours to 3 days, preferably 1 day to 2 days. If necessary, shaking, stirring and/or application of pressure may be added. Methods for shaking, stirring and/or application of pressure can be appropriately determined by the practitioner. For the amounts of the brown rice and the aqueous solvent, the aqueous solvent can be used in an amount selected from the range of 1 part by weight to 100 parts by weight, preferably 5 parts by weight to 80 parts by weight, more preferably 10 parts by weight to 50 parts by weight, per part by weight of the brown rice. For example, in the present invention, the aqueous solvent can be used in an amount of 10 parts by weight to 50 parts by weight per part by weight of the brown rice. For example, the aqueous solvent can be used in an amount of 300 mL to 3000 mL per 30 g to 60 g of the brown rice.

Together with the brown rice, the above yuzu seeds may be added to the aqueous solvent, and extracted in parallel as described above.

Subsequently, the mixture is subjected to solid-liquid separation, and the liquid part is recovered to obtain an aqueous solvent extract of brown rice. The solid-liquid separation can be performed by the above-described method. The resulting aqueous solvent extract of brown rice can be concentrated if necessary. The concentration of the extract can be performed by the above-described method. Further, the resulting aqueous solvent extract of brown rice can be dried or frozen if necessary. The drying of the extract can be performed by the above-described method.

3. Composition

The composition of the present invention contains an aqueous solvent extract of yuzu seeds and an aqueous solvent extract of brown rice.

The composition of the present invention can be obtained by mixing an aqueous solvent extract of yuzu seeds and an aqueous solvent extract of brown rice. The "mixing" of an aqueous solvent extract of yuzu seeds and an aqueous solvent extract of brown rice can be performed by combining and mixing the aqueous solvent extracts when the extracts are prepared separately. The mixing ratio of the aqueous solvent extract of yuzu seeds and the aqueous solvent extract of brown rice is not particularly limited, and the aqueous solvent extract of yuzu seeds and the aqueous solvent extract of brown rice can be mixed at a weight ratio selected from the range of 9 to 1:1 to 9, preferably at a weight ratio of 1:1.

Alternatively, the composition of the present invention can be obtained by subjecting yuzu seeds and brown rice to extraction using the same aqueous solvent. The term "extraction using the same aqueous solvent" means that extraction is performed sequentially or simultaneously using one aqueous solvent. Such extraction includes extraction of brown rice using an aqueous solvent extract of yuzu seeds as an aqueous solvent, extraction of yuzu seeds using an aqueous solvent extract of brown rice as an aqueous solvent, or extraction of yuzu seeds and brown rice by adding the yuzu seeds and the brown rice to an aqueous solvent at the same time. The extract obtained in this manner contains both the aqueous solvent extract of yuzu seeds and the aqueous solvent extract of brown rice.

In the composition of the invention, the aqueous solvent extract of yuzu seeds and the aqueous solvent extract of brown rice can be each incorporated in any amount. For example, the aqueous solvent extracts can be each incorporated in an amount of 0.00001 to 50 wt %, particularly about 0.0001 to 5 wt % in terms of a dry weight. For example, in the composition of the present invention, the aqueous solvent extracts can be each incorporated so as to meet a range of concentrations (ratios) that is defined when 100 mL to 2500 mL, preferably 300 mL to 1500 mL, of the composition contains the aqueous solvent extracts in an amount of 200 to 500 g, preferably 350 g, in terms of the amount (dry weight) of the yuzu seeds used for preparation of the aqueous solvent extract and in an amount of 10 to 50 g, preferably 30 g, in terms of the amount (dry weight) of the brown rice used for preparation of the aqueous solvent extract.

The composition of the present invention may be in the form of a pharmaceutical composition (including pharmaceutical products and quasi-pharmaceutical products) or a cosmetic composition.

When the composition of the present invention is a pharmaceutical composition, the dosage form is not particularly limited, and is preferably a dosage form that can be directly administered or applied to the skin, and examples thereof include external preparations such as ointments, solutions, lotions, creams, gels, emulsions and patches.

As long as the object, the action and the effect of the present invention are not impaired, ingredients that are commonly used for pharmaceutical products and quasi-pharmaceutical products can be appropriately selected, and added to the above-mentioned preparations together with the aqueous solvent extract of yuzu seeds and the aqueous solvent extract of brown rice which are active ingredients. Examples of the ingredients include, but are not limited to, excipients, binders, diluents, additives, fragrances, buffers, thickeners, colorants, stabilizers, emulsifiers, dispersants, disintegrants, suspending agents, surfactants and preservatives.

When the composition of the present invention is a cosmetic composition, the dosage form is not particularly limited, and is preferably a dosage form that can be directly administered or applied to the skin, and examples thereof include toners, cosmetic emulsions, serums, cosmetic creams, cosmetic gels, sheet masks, packs, foundations, lip balms, hand creams, facial cleansers and shower gels.

As long as the object, the action and the effect of the present invention are not impaired, ingredients that are commonly used for cosmetics can be appropriately selected, and added to the above-mentioned cosmetics together with the aqueous solvent extract of yuzu seeds and the aqueous solvent extract of brown rice which are active ingredients. Examples of the ingredients include, but are not limited to, surfactants, oils, moisturizing agents, softeners, sensory enhancers, oily agents, emulsifiers, antioxidants, preservatives, fungicides, emollient agents, pH adjusters, chelating agents, stabilizers, ultraviolet absorbers, alcohols, silicon compounds, thickeners, viscosity adjusters, solubilizers, pearling agents, fragrances, fresheners, bactericides, antibacterial agents, natural extracts, colorants, fading inhibitors, purified water and other solvents, and propellants.

4. Uses

The composition of the present invention is capable of producing an excellent moisturizing effect on the skin. The composition of the present invention has a high ability to penetrate the skin, and can enhance the moisture holding ability of the skin, so that the skin keeps moisture. In the skin, cells are renewed within a period of several weeks to a month. During this period, moisturization of the skin is maintained, and thus the skin environment is improved and/or maintained normal to enable treatment or relief, or alleviation or suppression of skin problems.

In the present invention, the term "treatment or relief, or alleviation or suppression" means not only a state in which skin problems completely disappear, but also a state in which temporarily or permanently, affected areas decrease in size or disappear, or symptoms are stable without being worsened (becoming advanced).

Examples of the disease whose condition or symptom is treated or relieved, or alleviated or suppressed by the composition of the present invention include dryness of skin, itching, acne, wrinkling and atopic dermatitis. The cause of itching is not particularly limited, and examples thereof include allergic dermatitis, dryness and insect bites. The disease whose condition or symptom is treated or relieved, or alleviated or suppressed by the composition of the present invention is especially preferably atopic dermatitis.

The composition of the present invention can produce an excellent moisturizing effect without causing inflammation even when an atopic dermatitis patient uses the composition. Application of the composition of the present invention to the affected areas of an atopic dermatitis patient eliminates itching from dryness in about 5 minutes, and use of the composition for about 3 days to 1 week enables suppression of inflammation itself. More specifically, the composition of the present invention is capable of the pH of the alkalified skin (having a pH of about 7 while the skin of a healthy person has a pH of about 4.5 to 6) of atopic dermatitis-affected areas back to normal by acidification, and holding moisture to suppress itching. If the skin has a high pH, i.e. the skin is alkalified, the skin is apt to dry, and form a hotbed of pathogenic bacteria such as *Staphylococcus aureus* which is one cause of inducing itching. When the skin is scratched, its barrier functions are damaged. When the skin's barrier functions are damaged, allergen penetrates the inside of the skin from outside, so that the itching is further worsened. As a result, the skin is further scratched, resulting in worsening of the symptom. When a steroid is applied here, neurotransmission causing an itching sensation is temporarily reduced, so that the itching symptom is eliminated on a temporary basis, but the skin's barrier functions are not normalized to the extent that moisture can be held, and inflammation occurs again. By applying the composition of the present invention to affected areas, the moisture holding ability of the skin is retained, and the pH balance of the skin can be improved and maintained to normalize the skin's barrier functions. Itching does not occur, therefore stress is relaxed. Because the skin is not scratched, the amount of external stimulus considerably decreases to promote restoration of the skin.

The composition of the present invention can also have effects such as prevention of skin roughness, production of beautiful skin, blood circulation promotion, metabolism promotion and promotion of waste product excretion.

The usage and dosage of the composition of the present invention can be appropriately determined in accordance with a conventional method on the basis of factors such as a target symptom, a target area or tissue, and a dosage form as long as it is possible to obtain an effect of treating or relieving, or alleviating or suppressing skin problems.

The composition of the present invention can be administered or applied over a long period of time, while enabling an effect to be obtained soon after administration/application (for example, immediately, within 1 minute, within 5 minutes, within 30 minutes or within 1 hour after administration or application). For example, the composition of the present invention can be continuously administered or applied over a 2 days or more, 3 days or more, 5 days or more, 1 week or more, 2 weeks or more, 3 weeks or more, 1 month or more, 2 months or more, or a longer period of time in accordance with the above-described usage and dosage. The composition of the present invention poses no or little side-effects even when continuously administered or applied.

The present invention will be described below by way of Examples, which should not be construed as limiting the scope of the present invention.

C.±1° C. for 96 hours. Here, solid components were removed to obtain an aqueous solvent extract of a yuzu seed whole and a germinated brown rice whole.

(2) Sensory Test

The extract was dropped to the skin of each of five subjects having atopic dermatitis, and thinly spread, and the reaction was observed.

Table 1 shows the results of sensory tests. As shown in Table 1, symptoms were improved in all the five subjects. There were not subjects that developed additional inflammation, or suffered from worsening of inflammation.

TABLE 1

| Subject | A | B | C | D | E |
|---|---|---|---|---|---|
| Sex | Male | Female | Female | Female | Female |
| Age | 38 years old | 41 years old | 28 years old | 27 years old | 28 years old |
| Occupation | Sales | Clerk | Sales | Clerk | Full-time housewife |
| Application area | Elbow, back side of knee, armpit, etc. | Face, neck, entire area below knee | Entire body | Face, body | Face |
| Time until itching subsides | About 5 minutes | About 10 minutes | About 30 minutes | about 60 minutes | About 30 minutes (no irritation) |
| Time until redness subsides | 2 days | 2 to 3 days (used once in the morning and once in the evening) | 2 to 3 days (used once in the morning and twice in the evening) | Face: 3 days Body: there was no redness, and dryness subsided after about 1 week | 5 days to 1 week (used once in the morning and once in the evening) |
| Remarks | | Hardening of skin from atopic dermatitis | | Hardening of skin from atopic dermatitis | Hardening of skin from atopic dermatitis |

EXAMPLES

Example 1: Composition Containing Aqueous Solvent Extract of Yuzu Seeds and Germinated Brown Rice (1) Preparation of Extract Seeds taken out from yuzu fruit and dried once were used without being washed. The yuzu seeds used were whole seeds (yuzu seed whole) which were not ground or cut. 350 g of the yuzu seed whole was immersed in 1500 mL of a 20% ethanol aqueous solution, and stored in a thermostatic bath at 5° C.±1° C. for 96 hours. Thereafter, solid components were removed to obtain an aqueous solvent extract of a yuzu seed whole.

30 g of brown rice was added to 300 mL of purified water without being washed with water, and was stored in a thermostatic bath at 37° C.±1° C. for about 48 hours until germination while the water was renewed as appropriate. Subsequently, the germinated brown rice was taken out, and the whole germinated brown rice (germinated brown rice whole) was added to the aqueous solvent extract of a yuzu seed whole (1500 mL) without being ground or cut. The resulting mixture was stored in a thermostatic bath at 5°

Example 2: Composition Containing Aqueous Solvent Extract of Yuzu Seed Whole and Non-Germinated Brown Rice Whole (1) Preparation of Extract Seeds taken out from yuzu fruit and dried once were used without being washed. The yuzu seeds used were whole seeds (yuzu seed whole) which were not ground or cut. 350 g of the dried yuzu seed whole was immersed in 1500 mL of a 20% ethanol aqueous solution, and stored in a thermostatic bath at 5° C.±1° C. for 96 hours. Thereafter, solid components were removed to obtain an aqueous solvent extract of a yuzu seed whole.

30 g of brown rice was added to 300 mL of purified water without being washed with water, and was stored in a thermostatic bath at 37° C.±1° C. until immediately before germination (for about 40 to 48 hours). Subsequently, the brown rice immediately before germination was taken out, and the whole brown rice (non-germinated brown rice whole) was added to the aqueous solvent extract of a yuzu seed whole (1500 mL) without being ground or cut. The resulting mixture was stored in a thermostatic bath at 5° C.±1° C. for 96 hours. Subsequently, solid components were removed to obtain an aqueous solvent extract of a yuzu seed whole and a non-germinated brown rice whole.

(2) Sensory Test on Ingredients (Skin Surface Horny Layer Moisture Content)

(2-1) Procedure

The skin surface horny layer moisture content was measured with a moisture meter (SKICON-200EX manufactured by Yayoi Co., Ltd.) before application of the following extracts A to E to the back of the hand of a subject, immediately after the application, 60 seconds after the application, 90 seconds after the application, 5 minutes after the application and 30 minutes after the application.

The following extract A was applied to the back of the hand of the subject for consecutive 14 days once in the morning and once in the evening a day. The skin surface horny layer moisture content was similarly measured.

(2-2) Extracts

A: Aqueous solvent extract of a yuzu seed whole and a non-germinated brown rice whole (prepared in the production method in (1)).

B: Aqueous solvent extract prepared in the same manner as in the production method in (1) except that the brown rice whole (dry weight: 30 g) immediately before germination was added to a 20% ethanol aqueous solution (1500 mL) instead of the aqueous solvent extract of a yuzu seed whole, the resulting mixture was stored in a thermostatic bath at 5° C. for 96 hours, and solid components were removed.

C: Aqueous solvent extract of a yuzu seed whole that was prepared in the production method in (1).

D: Aqueous solvent extract prepared in the same manner as in the production method in (1) except that the brown rice whole (dry weight was increased to 50 g) immediately before germination was added to a 20% ethanol aqueous solution (1500 mL) instead of the aqueous solvent extract of a yuzu seed whole, the resulting mixture was stored in a thermostatic bath at 5° C. for 96 hours, and solid components were removed.

E: Aqueous solvent extract of a yuzu seed whole that was prepared in the same manner as in the production method in (1) except that the amount of the dried yuzu seed whole used was increased from 350 g to 500 g.

(2-3) Subjects

Subjects were 18 people (7 males and 11 females) between the ages of 19 and 71.

(2-4) Results

FIG. 1(I) shows the results (expressed as average values) of measuring the skin surface horny layer moisture content before application of the extracts A to E to the back of the hand of the subject, immediately after the application, 60 seconds after the application, 90 seconds after the application, 5 minutes after the application and 30 minutes after the application.

When the aqueous solvent extract of a yuzu seed whole and a non-germinated brown rice whole (A) was used, a significantly higher horn moisture holding ability was exhibited as compared to each of the other extracts (B, C, D and E) until the end of the 30-minute test from immediately after application, and it was indicated that a combination of an aqueous solvent extract of a non-germinated brown rice whole and an aqueous solvent extract of a yuzu seed whole had a synergistic effect.

FIG. 1(II) shows the results (expressed as average values) of measuring the skin surface horny layer moisture content before application of the aqueous solvent extract of a yuzu seed whole and a non-germinated brown rice whole (A) to the back of the hand of the subject after continuously using the extract A, immediately after the application, 60 seconds after the application, 90 seconds after the application, 5 minutes after the application and 30 minutes after the application.

Comparison between the skin surface horny layer moisture content before and that after the continuous use of the aqueous solvent extract of a yuzu seed whole and a non-germinated brown rice whole (A) showed that immediately after the application, there was no significant difference between the both, but before the application and after the elapse of a time after the application, the skin surface horny layer moisture content after the continuous use was significantly higher. This result shows that continuous use of the aqueous solvent extract of a yuzu seed whole and a non-germinated brown rice whole (A) enhanced the moisture absorption ability and the moisture holding ability of the skin surface horny layer.

(3) Sensory Test on Symptoms (3-1) Procedure

The following extracts a to e and purified water (f) were applied twice a day to relevant affected areas of subjects having symptoms (i) to (v). After 1 day, after 5 days, after 1 week, after 1 month and after 2 months, the effect was rated on the following 5-point scale.

5: Remarkably effective (affected areas shrink or decrease in size by about 30% or more)
4: Effective (affected areas shrink or decrease in size by less than about 30%)
3: No change
2: Slightly worsened (affected areas expand or increase in size by less than about 30%)
1: Worsened (affected areas expand or increase in size by about 30% or more)

The skin surface horny layer moisture content was measured with a moisture meter (SKICON-200EX manufactured by Yayoi Co. Ltd.) before application of a to f to relevant affected areas of subjects having (i) dryness of skin, immediately after the application, 60 seconds after the application, 90 seconds after the application, 5 minutes after the application and 30 minutes after the application.

Further, the skin pH was measured before application of a to f to relevant affected areas of subjects having (iii) atopic dermatitis, and 5 minutes after the application.

(3-2) Extracts a: Aqueous solvent extract of a non-germinated brown rice whole (30 g of brown rice was added to 300 mL of purified water without being washed with water, and was stored in a thermostatic bath at 37° C. until immediately before germination (for about 48 hours). Subsequently, the non-germinated brown rice immediately before germination was taken out, added to 1500 mL of a 20% ethanol aqueous solution, and stored in a thermostatic bath at 5° C. for 96 hours, and solid components were then removed to obtain an aqueous solvent extract.)

b: Aqueous solvent extract of a germinated brown rice whole (30 g of brown rice was added to 300 mL of purified water without being washed with water, and was stored in a thermostatic bath at 37° C. until germination. Subsequently, the germinated brown rice was taken out, added to 1500 mL of a 20% ethanol aqueous solution, and stored in a thermostatic bath at 5° C. for 96 hours, and solid components were then removed to obtain an aqueous solvent extract.)

c: Aqueous solvent extract of a yuzu seed whole that was prepared in the production method in (1).

d: Extract obtained by grinding and squeezing yuzu seeds, and then removing solid components (hereinafter, referred to as a "yuzu seed oil")

e: Aqueous solvent extract of a yuzu seed whole and a non-germinated brown rice whole (prepared in the production method in (1))

f: Purified water (3-3) Subjects (i) Dry skin: 12 subjects (skin surface horny layer moisture content in back of hand: 100 μS or less; 3 subjects have xeroderma with a hardened horn or scratched scar)

(ii) Itching: 12 subjects (all diagnosed as allergic dermatitis in medical settings)
(iii) Atopic dermatitis: 12 subjects (5 subjects had a marked thickening, lichened lesion and erosion)
(iv) Acne: 10 subjects (subjects having 15 or more visible comedos on the face)
(v) Wrinkling: 12 subjects (subjects having palpable nasolabial lines and forehead wrinkles)

(3-4) Results

Tables 2, 3 and 4 show the results (expressed as average values) of applying the extracts a to e and purified water (f) to affected areas, and evaluating effects after 1 day, after 5 days, after 1 week, after 1 month and after 2 months.

Table 2 shows the results of comparing the aqueous solvent extract of a non-germinated brown rice whole (a), the aqueous solvent extract of a germinated brown rice whole (b) and purified water (f).

For the "dry skin", the aqueous solvent extract of a non-germinated brown rice whole (a) and the aqueous solvent extract of a germinated brown rice whole (b) both exhibited a significantly higher value as compared to the purified water (f) (P<0.05, t-test) at the end of the 2-month test. On the other hand, comparison of the aqueous solvent extract of a non-germinated brown rice whole (a) with the aqueous solvent extract of a germinated brown rice whole (b) showed that there was no significant difference between these extracts.

For the "itching", at the end of the 2-month test, the aqueous solvent extract of a non-germinated brown rice whole (a) exhibited a significantly higher value as compared to the purified water (f) (P<0.05, t-test), and there was no significant difference between the aqueous solvent extract of a germinated brown rice whole (b) and the purified water (f). Comparison of the aqueous solvent extract of a non-germinated brown rice whole (a) with the aqueous solvent extract of a germinated brown rice whole (b) showed that the aqueous solvent extract of a non-germinated brown rice whole (a) exhibited a significantly higher value (P<0.05, t-test) after 5 days and beyond.

For the "atopic dermatitis", at the end of the 2-month test, the aqueous solvent extract of a non-germinated brown rice whole (a) exhibited a significantly higher value as compared to the purified water (f) (P<0.05, t-test), and there was no significant difference between the aqueous solvent extract of a germinated brown rice whole (b) and the purified water (f). Comparison of the aqueous solvent extract of a non-germinated brown rice whole (a) with the aqueous solvent extract of a germinated brown rice whole (b) showed that the aqueous solvent extract of a non-germinated brown rice whole (a) exhibited a significantly higher value after 1 week, and the aqueous solvent extract of a non-germinated brown rice whole (a) exhibited a significantly higher value (P<0.05, t-test) even after 2 months.

For the "acne", the aqueous solvent extract of a non-germinated brown rice whole (a) and the aqueous solvent extract of a germinated brown rice whole (b) both exhibited a significantly higher value as compared to the purified water (f) (P<0.05, t-test) at the end of the 2-month test. On the other hand, comparison of the aqueous solvent extract of a non-germinated brown rice whole (a) with the aqueous solvent extract of a germinated brown rice whole (b) showed that there was no significant difference between these extracts.

For the "wrinkling", the aqueous solvent extract of a non-germinated brown rice whole (a) and the aqueous solvent extract of a germinated brown rice whole (b) both exhibited a significantly higher value as compared to the purified water (f) (P<0.05, t-test) at the end of the 2-month test. On the other hand, comparison of the aqueous solvent extract of a non-germinated brown rice whole (a) with the aqueous solvent extract of a germinated brown rice whole (b) showed that there was no significant difference between these extracts.

As described above, comparison of the aqueous solvent extract of a non-germinated brown rice whole (a) with the aqueous solvent extract of a germinated brown rice whole (b) showed that the aqueous solvent extract of a non-germinated brown rice whole (a) was more effective against "itching" and "atopic dermatitis".

TABLE 2

Comparison of aqueous solvent extract of non-germinated brown rice whole with aqueous solvent extract of germinated brown rice whole

|   | After 1 day | After 5 days | After 1 week | After 1 month | After 2 months |
|---|---|---|---|---|---|
| (i) Dry skin: 12 subjects | | | | | |
| a | 3.5 | 3.8 | 4.0 | 4.0 | 4.3 |
| b | 3.5 | 4.0 | 4.0 | 4.3 | 4.3 |
| f | 2.7 | 2.6 | 2.2 | 2.5 | 2.7 |
| (ii) Itching: 12 subjects | | | | | |
| a | 3.7 | 3.8 | 3.8 | 4.1 | 4.2 |
| b | 3.5 | 3.5 | 3.1 | 3.1 | 2.8 |
| f | 2.7 | 2.5 | 2.7 | 2.7 | 2.7 |
| (iii) Atopic dermatitis: 12 subjects | | | | | |
| a | 3.5 | 3.3 | 3.3 | 3.1 | 3.2 |
| b | 3.5 | 3.1 | 2.7 | 2.4 | 2.4 |
| f | 2.4 | 2.4 | 2.6 | 2.5 | 2.5 |
| (iv) Acne: 10 subjects | | | | | |
| a | 3.0 | 3.1 | 3.6 | 3.8 | 4.0 |
| b | 3.0 | 3.1 | 3.8 | 3.8 | 4.1 |
| f | 3.0 | 3.0 | 2.6 | 2.5 | 2.5 |
| (v) Wrinkling: 12 subjects | | | | | |
| a | 3.1 | 3.2 | 3.3 | 3.3 | 3.5 |
| b | 3.1 | 3.2 | 3.4 | 3.4 | 3.6 |
| f | 3.0 | 3.0 | 3.1 | 3.0 | 3.0 |

Table 3 shows the results of comparing the aqueous solvent extract of a yuzu seed whole (c), the yuzu seed oil (d) and the purified water (f).

For the "dry skin", the aqueous solvent extract of a yuzu seed whole (c) and the yuzu seed oil (d) both exhibited a significantly higher value as compared to the purified water (f) (P<0.05, t-test) at the end of the 2-month test. On the other hand, comparison of the aqueous solvent extract of a yuzu seed whole (c) with the yuzu seed oil (d) showed that the aqueous solvent extract of a yuzu seed whole (c) exhibited a significantly higher value (P<0.05, t-test) after 1 month.

For the "itching", the aqueous solvent extract of a yuzu seed whole (c) and the yuzu seed oil (d) both exhibited a significantly higher value as compared to the purified water (f) (P<0.05, t-test) at the end of the 2-month test. On the other hand, comparison of the aqueous solvent extract of a yuzu seed whole (c) with the yuzu seed oil (d) showed that there was no significant difference between them.

For the "atopic dermatitis", the aqueous solvent extract of a yuzu seed whole (c) and the yuzu seed oil (d) both exhibited a significantly higher value as compared to the purified water (f) (P<0.05, t-test) at the end of the 2-month test. On the other hand, comparison of the aqueous solvent extract of a yuzu seed whole (c) with the yuzu seed oil (d)

showed that the aqueous solvent extract of a yuzu seed whole (c) exhibited a significantly higher value (P<0.05, t-test) at the end of the 2-month test period.

For the "wrinkling", at the end of the 2-month test, the aqueous solvent extract of a yuzu seed whole (c) exhibited a significantly higher value as compared to the purified water (f) (P<0.05, t-test), and there was no significant difference between the yuzu seed oil (d) and the purified water (f). Comparison of the aqueous solvent extract of a yuzu seed whole (c) with the yuzu seed oil (d) showed that the aqueous solvent extract of a yuzu seed whole (c) exhibited a significantly higher value (P<0.05, t-test) after 1 week and beyond.

For the "acne", the aqueous solvent extract of a yuzu seed whole (c) and the yuzu seed oil (d) both exhibited a significantly higher value as compared to the purified water (f) (P<0.05, t-test) at the end of the 2-month test. On the other hand, comparison of the aqueous solvent extract of a yuzu seed whole (c) with the yuzu seed oil (d) showed that there was no significant difference between them.

As described above, comparison of the aqueous solvent extract of a yuzu seed whole (c) with the yuzu seed oil (d) showed that the aqueous solvent extract of a yuzu seed whole (c) was more effective against "dryness", "atopic dermatitis" and "wrinkling".

TABLE 3

Comparison of aqueous solvent extract of yuzu seed whole with yuzu seed oil

|   | After 1 day | After 5 days | After 1 week | After 1 month | After 2 months |
|---|---|---|---|---|---|
| (i) Dry skin: 12 subjects | | | | | |
| c | 3.5 | 3.7 | 3.8 | 4.0 | 4.0 |
| d | 3.5 | 3.5 | 3.7 | 3.7 | 3.8 |
| f | 2.7 | 2.6 | 2.2 | 2.5 | 2.7 |
| (ii) Itching: 12 subjects | | | | | |
| c | 3.8 | 3.8 | 4.1 | 4.2 | 4.2 |
| d | 3.7 | 3.7 | 3.8 | 3.7 | 4.0 |
| f | 2.7 | 2.5 | 2.7 | 2.7 | 2.7 |
| (iii) Atopic dermatitis: 12 subjects | | | | | |
| c | 3.8 | 4.1 | 4.2 | 4.3 | 4.4 |
| d | 3.5 | 3.8 | 3.8 | 4.1 | 4.1 |
| f | 2.4 | 2.4 | 2.6 | 2.5 | 2.5 |
| (iv) Acne: 10 subjects | | | | | |
| c | 3.0 | 3.2 | 3.2 | 3.2 | 3.5 |
| d | 3.0 | 3.2 | 3.0 | 3.2 | 3.2 |
| f | 3.0 | 3.0 | 2.6 | 2.5 | 2.5 |
| (v) Wrinkling: 12 subjects | | | | | |
| c | 3.1 | 3.2 | 3.9 | 4.0 | 4.2 |
| d | 3.1 | 3.2 | 3.2 | 3.2 | 3.3 |
| f | 3.0 | 3.0 | 3.1 | 3.0 | 3.0 |

Table 4 shows the results of using an aqueous solvent extract of a yuzu seed whole and a non-germinated brown rice whole (e). When the aqueous solvent extract of a yuzu seed whole and a non-germinated brown rice whole (e) was used, a significantly higher value was exhibited as compared to the purified water (f) (P<0.05, t-test) at the end of the 2-month test for all the "dry skin", "itching", "atopic dermatitis", "acne" and "wrinkling". In particular, for the "itching" and the "atopic dermatitis", a significantly higher value was exhibited after 1 day and beyond as compared to when each of the ingredients a, b, c and d was used singly. It was revealed that the aqueous solvent extract of a yuzu seed whole and a non-germinated brown rice whole (e) produced an early and high improving effect.

TABLE 4

Aqueous solvent extract of yuzu seed whole and non-germinated brown rice whole

|   | After 1 day | After 5 days | After 1 week | After 1 month | After 2 months |
|---|---|---|---|---|---|
| (i) Dry skin: 12 subjects | | | | | |
| e | 4.1 | 4.2 | 4.4 | 4.5 | 4.6 |
| (ii) Itching: 12 subjects | | | | | |
| e | 4.7 | 4.7 | 4.8 | 5.0 | 5.0 |
| (iii) Atopic dermatitis: 12 subjects | | | | | |
| e | 4.1 | 4.4 | 4.6 | 4.6 | 4.9 |
| (iv) Acne: 10 subjects | | | | | |
| e | 3.0 | 3.2 | 3.7 | 4.2 | 4.5 |
| (v) Wrinkling 12 subjects | | | | | |
| e | 3.5 | 4.0 | 4.1 | 4.3 | 4.6 |

It is confirmed that application of the aqueous solvent extract of a yuzu seed whole and a non-germinated brown rice whole (e) improved the symptoms as follows.

(Dry Skin)
Upon application, the extract was soon absorbed into the skin to expand the skin from the inside.
Inflammation subsided, so that the skin became fine-textured.
Xeroderma worsened by steroid therapy was completely healed.

(Itching)
An itching sensation developed on the entire face by allergic reaction from hay fever subsided immediately after application.
Rashes and sores completely subsided.
Itching caused by an insect bite subsided, and did not relapse.

(Atopic Dermatitis)
Atopic dermatitis advanced to the extent that the level of prescribed steroids was "Very Strong" completely subsided.
Scales were eliminated, so that the skin became smooth.
Pigment deposits on scratch scars disappeared, and the itching symptom was eliminated.

(Acne)
Upon application, development of comedos soon subsided, and declined in about 2 weeks. The symptom almost completely subsided in 3 months.
Redness subsided, and acne scars disappeared.
There was no longer excess sebum.

(Wrinkling)
Wrinkles around the eyes and neck wrinkles completely disappeared.
Deep wrinkles became shallower.
Sagging was improved, and the skin became more elastic.

Figure 2:
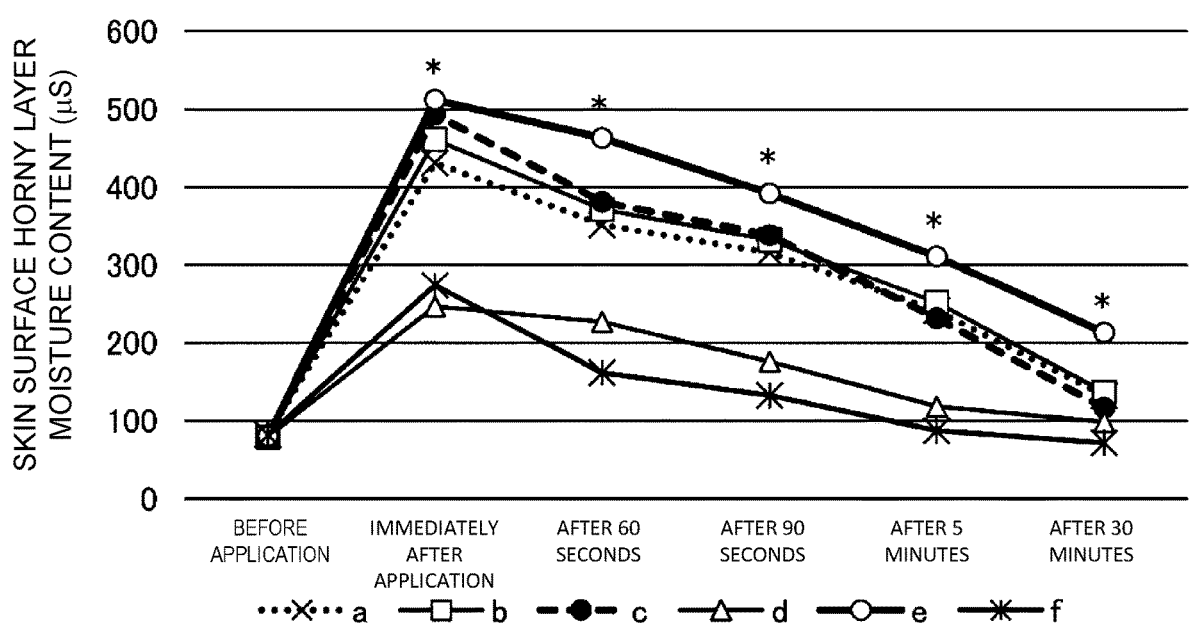
FIG. 2 is a graph chart showing the results of measuring the skin surface horny layer moisture content before and after application of extracts a to f, where a is an aqueous solvent extract of a non-germinated brown rice whole, b is an aqueous solvent extract of a germinated brown rice whole, c is an aqueous solvent extract of a yuzu seed whole, d is a yuzu seed oil, e is an aqueous solvent extract of a yuzu seed whole and a non-germinated brown rice whole and f is purified water (*: P<0.05 (vs each of a, b, c, d and f), t-test).

Further, FIG. 2 shows the results (expressed as average values) of measuring the skin surface horny layer moisture content before application of a to f to affected areas with relevant symptoms in subjects having (i) dry skin, immediately after the application, 60 seconds after the application, 90 seconds after the application, 5 minutes after the application and 30 minutes after the application.

When the aqueous solvent extract of a yuzu seed whole and a non-germinated brown rice whole (e) was used, a significantly higher horn moisture holding ability was exhibited as compared to each of the other extracts (a, b, c and d) and the purified water (f) until the end of the 30-minute test from immediately after application, and it was confirmed that a combination of an aqueous solvent extract of a non-germinated brown rice whole and an aqueous solvent extract of a yuzu seed whole had a synergistic effect.

Further, Table 5 below shows the results (expressed as average values) of measuring the skin pH before application of a to f to affected areas with relevant symptoms in subjects having (iii) atopic dermatitis, and 5 minutes after the application. It was confirmed that application of the aqueous solvent extract of a yuzu seed whole (c) and the aqueous solvent extract of a yuzu seed whole and a non-germinated brown rice whole (e) considerably reduced the skin pH value (acidified the skin).

TABLE 5

|   | Extract pH | Skin pH Before application | Skin pH 5 minutes after application |
|---|---|---|---|
| a | 6.0 | 7.1 | 6.7 |
| b | 6.0 | 7.1 | 6.8 |
| c | 3.0 | 7.1 | 5.8 |
| d | 4.0 | 7.1 | 6.3 |
| e | 3.0 | 7.1 | 5.8 |

In general, the skin pH of affected areas from atopic dermatitis represents an alkalified environment. Growth of pathogenic bacteria such as *Staphylococcus aureus* in the alkaline environment causes development and/or worsening of atopic dermatitis. Reduction of the skin pH value by application of the aqueous solvent extract of a yuzu seed whole (c) and the aqueous solvent extract of a yuzu seed whole and a non-germinated brown rice whole (e) may be one of factors of improving the symptoms of atopic dermatitis.

Since the skin with atopic dermatitis is extremely dry, improvement in dry skin is also required for improvement in this symptom. It was confirmed that the aqueous solvent extract of a non-germinated brown rice whole (a) and the aqueous solvent extract of a germinated brown rice whole (b) were effective for improvement in the symptom of dry skin as described above. However, when considering application to atopic dermatitis (Table 2 above), use of the aqueous solvent extract of a non-germinated brown rice whole (a), which is more effective against "itching" and "atopic dermatitis", is the most suitable. Thus, the aqueous solvent extract of a yuzu seed whole and a non-germinated brown rice whole (e) is considered to be an extremely effective combination for improving atopic dermatitis.

Example 3: Formulation Example of Cosmetics

Formulation examples of cosmetics containing the aqueous solvent extract of a yuzu seed whole and a non-germinated brown rice whole according to the present invention will be shown below. All the percentages are weight percentages (wt %). All the cosmetics are prepared at room temperature.

(Formulation Example 1) Toner

| Extract | 95.0% |
|---|---|
| Glycerin | 4.5% |
| 1,3-Butylene glycol | 0.5% |
| Fragrance | appropriate |

(Formulation Example 2) Lotion

| Extract | 95.0% |
|---|---|
| Squalane | 0.2% |
| Tween 80 | 0.1% |
| Span 80 | 0.1% |
| Fragrance | appropriate |
| Purified water | balance |

(Formulation Example 3) Cream

| Extract | 95.0% |
|---|---|
| Oleic acid | 70.0% |
| Squalane | 20.0% |
| Tween 80 | 2.0% |
| Span 80 | 2.0% |
| Fragrance | appropriate |
| Purified water | balance |

The invention claimed is:

1. A topical composition comprising an effective amount of a mixture of an aqueous solvent extract of yuzu seeds and an aqueous solvent extract of brown rice;
    wherein the extract of brown rice is obtained from brown rice immediately before germination and the brown rice has an expanded germ;
    wherein the composition is a pharmaceutical composition or a cosmetic composition in a dosage form formulated to be directly administered or applied to skin, and wherein said dosage form is selected from the group consisting of ointments, lotions, creams, gels, emulsions, patches, cosmetic emulsions, cosmetic creams, cosmetic gels, sheet masks, packs, lip balms, hand creams, and shower gels.

2. The composition according to claim 1, wherein the aqueous solvent is one or a combination of two or more selected from the group consisting of water and alcohols.

3. The composition according to claim 1, wherein the composition is a pharmaceutical composition, which is an external preparation.

4. The composition according to claim 1, wherein the composition is a cosmetic composition.

5. A method for producing the topical composition of claim 1, the method comprising the steps of: extracting yuzu seeds with an aqueous solvent to obtain an aqueous solvent extract; and extracting brown rice with an aqueous solvent to obtain an aqueous solvent extract and combining into a dosage form.

6. The method according to claim 5, comprising the steps of:
    extracting yuzu seeds with an aqueous solvent to obtain an aqueous solvent extract; and
    extracting brown rice with the aqueous solvent extract to obtain an extraction liquid.

7. The method according to claim 5, wherein the brown rice is brown rice immediately before germination.

8. The method according to claim 5, wherein the aqueous solvent is one or a combination of two or more selected from the group consisting of water and alcohols.

9. A method for treating or relieving a skin problem comprising administering an effective amount of the topical composition of claim 1 to a subject in need thereof.

10. The method according to claim 9, wherein the skin problem is dryness of skin.

11. The method according to claim 9, wherein the skin problem is itching of skin.

12. The method according to claim 9, wherein the skin problem is acne.

13. The method according to claim 9, wherein the skin problem is atopic dermatitis.

14. The method according to claim 9, wherein the skin problem is wrinkling.

15. The method according to claim 9, wherein the brown rice is brown rice immediately before germination.

16. The method according to claim 9, wherein the aqueous solvent is one or a combination of two or more selected from the group consisting of water and alcohols.

\* \* \* \* \*